United States Patent

Hall

(10) Patent No.: US 6,413,912 B2
(45) Date of Patent: *Jul. 2, 2002

(54) AZOLINE DERIVATIVES

(75) Inventor: Roger Graham Hall, Pfeffingen (CH)

(73) Assignee: Syngenta Crop Protection, Inc., Greensboro, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/530,638

(22) PCT Filed: Nov. 2, 1998

(86) PCT No.: PCT/EP98/06915

§ 371 (c)(1), (2), (4) Date: May 3, 2000

(87) PCT Pub. No.: WO99/23081

PCT Pub. Date: May 14, 1999

(30) Foreign Application Priority Data

Nov. 4, 1997 (CH) .............................................. 2548/97

(51) Int. Cl.⁷ .......................... A01N 43/76; A01N 43/78; C07D 263/10; C07D 277/10
(52) U.S. Cl. ........................ 504/266; 504/270; 548/146; 548/239
(58) Field of Search ................... 548/146, 239; 504/266, 270

(56) References Cited

U.S. PATENT DOCUMENTS

| | | | |
|---|---|---|---|
| 5,578,625 A | 11/1996 | Suzuki et al. | 514/374 |
| 5,807,877 A | 9/1998 | Lantzsch et al. | 514/374 |
| 5,969,147 A | 10/1999 | Lantzsch et al. | 548/237 |
| 5,973,162 A | * 10/1999 | Alig et al. | 548/203 |
| 6,051,589 A | 4/2000 | Kanellakopulos et al. | 514/374 |

FOREIGN PATENT DOCUMENTS

| | | |
|---|---|---|
| DE | 195 23 388 | 4/1996 |
| DE | 195 15 296 A1 | 10/1996 |
| DE | 195 15 297 A1 | 10/1996 |
| DE | 19548419 | * 6/1997 |
| EP | 0 345 775 | 12/1989 |
| EP | 432661 | * 6/1991 |
| EP | 0 686 345 | 12/1995 |
| EP | 0 696 584 | 2/1996 |
| JP | 09059115 A | 8/1995 |
| WO | WO 93/25079 | 12/1993 |
| WO | WO 95/04726 | 2/1995 |
| WO | WO 95/19350 | 7/1995 |
| WO | WO 96/11190 | 4/1996 |
| WO | WO 96/18619 | 6/1996 |
| WO | WO 96/22283 | 7/1996 |
| WO | WO 96/41534 | 12/1996 |
| WO | WO 97/13773 | 4/1997 |
| WO | WO 97/19067 | 5/1997 |
| WO | WO 97/23468 | 7/1997 |
| WO | WO 97/26249 | 7/1997 |

OTHER PUBLICATIONS

Derwent Abstract 97–209188/19 (abstract of JP 09059115–A), 1995.
Derwent Abstract 1997–035173/199704 (of WO 96/41534), 1996.
Derwent Abstract 1996–486342/199649 (of DE 19515296), 1996.
Derwent Abstract 1996–486343/199649 (of DE 19515297), 1996.
Derwent Abstract 1996–287619/199630 (of WO 96/18619), 1996.
Derwent Abstract 1997–282450/199726 (of WO 97/19067), 1997.
Derwent Abstract 1998–569605/199849 (of WO 98/47881), 1998.

* cited by examiner

*Primary Examiner*—Laura L. Stockton
(74) *Attorney, Agent, or Firm*—William A. Teoli, Jr.

(57) ABSTRACT

Trifluoromethylbiphenylyl-dihalophenylazolines of formula I

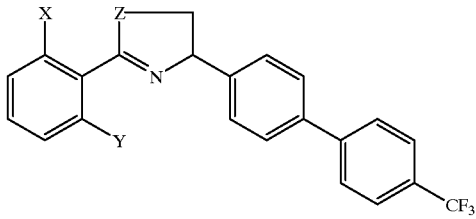

wherein X and Y are, independently fluorine or chlorine, and Z is O or S, their tautomers and salts are disclosed which are useful as pesticides. Compositions of these compounds of these compounds, their use in pesticidal applications, methods of manufacture thereof and intermediates in the manufacturing process are also disclosed.

13 Claims, No Drawings

AZOLINE DERIVATIVES

This application is a 371 of PCT/EP98/06915 filed Nov. 2, 1998.

The object of the invention is a compound of formula

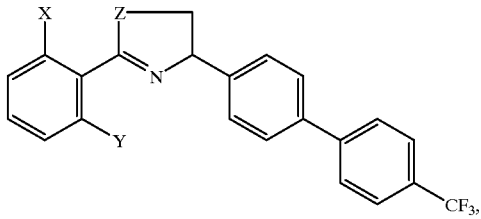

(I)

wherein X and Y are, independently of one another, fluorine or chlorine, and Z is O or S;
and where appropriate their possible tautomers, in each case either in free form or in the form of a salt; a method for the preparation and application of these compounds, their salts and their tautomers; pesticides whose active ingredient is selected from these compounds and their tautomers; and a method for the preparation and application of these compositions, intermediates, in free form or in the form of a salt, for the preparation of these compounds, where appropriate tautomers, in free form or in the form of a salt.

In the literature, certain oxazoline derivatives are proposed as insecticidally active substances in pesticides. The biological properties of these known compounds, however, are not fully satisfactory in the field of pest control, which is why there is a need to produce further compounds with pesticidal properties, especially for the control of insects; this problem is solved according to the invention with the development of the present compounds of formula (I).

The compounds of formula (I) may be present partly in the form of tautomeric derivatives. Accordingly, any reference to compounds of formula (I) hereinbefore and hereinafter is understood to include also their corresponding tautomers, even if the latter are not specifically mentioned in each case.

The compounds of formula (I) and where appropriate their tautomers can form salts, for example acid addition salts. These are formed for example with strong inorganic acids, typically mineral acids, e.g. sulfuric acid, a phosphoric acid or a halogen acid, or with strong organic carbonic acids, typically $C_1$-$C_4$alkanecarbonic acids substituted where appropriate for example by halogen, e.g. acetic acid, such as dicarbonic acids that are unsaturated where necessary, e.g. oxalic, malonic, maleic, fumaric or phthalic acid, typically hydroxycarbonic acids, e.g. ascorbic, lactic, malic, tartaric or citric acid, or benzoic acid, or with organic sulfonic acids, typically $C_1$-$C_4$alkane or arylsulfonic acids substituted where appropriate for example by halogen, e.g. methanesulfonic or p-toluenesulfonic acid. In a broader sense, compounds of formula (I) with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Furthermore, where appropriate corresponding internal salts may also be formed. The free form is preferred. Among the salts of compounds of formula (I), the agrochemically beneficial salts are preferred. Hereinbefore and hereinafter, the free compounds of formula (I) and their salts are understood where appropriate to include also by analogy the corresponding salts or free compounds of formula (I). The same applies for tautomeric derivatives of compounds of formula (I) and salts thereof.

Compounds of formula (I), wherein X and Y are fluorine, are preferred. Likewise preferred are compounds of formula (I), wherein Z is O.

The individual compounds of this claim according to the invention are preferably (1) 2-(2,6-Dichlorophenyl)-4-(4'-trifluoromethylbiphenyl-4yl)-4,5-dihydro-oxazole; or (2) 2-(2,6-Chloro,6-fluorophenyl)-4-(4'-trifluoromethylbiphenyl-4-yl)-4,5-dihydro-oxazole; or (3) 2-(2,6-Difluorophenyl)-4-(4'-trifluoromethylbiphenyl-4-yl)-4,5-dihydro-oxazole.

A further object of the invention is a method for preparing the compounds of formula (I) and where appropriate their tautomers, in each case in free form or in the form of a salt, comprising a) the reaction of a compound of formula

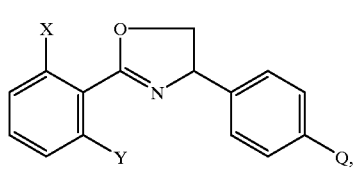

(II)

which is known or can be prepared according to known methods, and wherein X and Y are as defined for formula (I) and Q is bromine or iodine, with a compound of formula

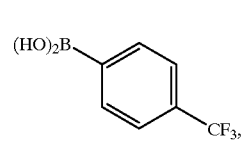

(III)

which is known; and b) where appropriate, for preparing a compound of formula (I), wherein Z is S, the reaction of the resulting compound of formula (I), wherein Z is O, with Lawesson's reagent [2,4-bis(methoxyphenyl)-1,3-dithia-2,4-diphosphetane-2,4-disulfide] or with phosphorus pentasulfide;

and in each case, if so desired, the conversion of a compound of formula (I) obtainable according to the method or by other means, or a tautomer thereof, present in free form or in the form of a salt, into a different compound of formula (I) or a tautomer thereof, the separation of a mixture of isomers obtainable according to the method and isolation of the desired isomer and/or the conversion of a free compound of formula (I) obtainable according to the method, or a tautomer thereof, into a salt, or a salt obtainable according to the method from a compound of formula (I), or a tautomer thereof, into the free compound of formula (I), or a tautomer thereof, or into a different salt.

The statement made hereinabove with regard to tautomers and salts of formula (I) apply by analogy in respect of the tautomers and salts of starting materials mentioned hereinbefore and hereinafter.

The reactions described hereinbefore and hereinafter are carried out in a known manner, e.g. in the absence or usually in the presence of a suitable solvent or diluent or a mixture thereof, proceeding as required under conditions of cooling, of ambient temperature, or of heating, e.g. in a temperature range of about −80° C. to the boiling temperature of the reaction medium, preferably about 0° C. to about +150° C., and where appropriate in a closed vessel, under pressure, in an inert gas atmosphere, and/or under non-aqueous conditions. Especially advantageous reaction conditions are described in the Examples.

The starting materials listed hereinbefore and hereinafter for the preparation of compounds of formula (I) and where appropriate the tautomers thereof, either in free form or in the form of a salt, are known or can be prepared according to known methods, e.g. as described hereinafter.

Variant a):

Suitable catalysts are in particular transition metal catalysts, especially iron, palladium, ruthenium, rhodium, nickel, zinc, or platinum catalysts. Particularly suitable are iron(I), nickel(0) and palladium(0) catalysts, especially $Pd(PPh_3)_4$.

Suitable bases for facilitating the reaction are e.g. alkali metal or alkaline earth metal hydroxides, hydrides, amides, alkanolates, acetates, carbonates, dialkylamides or alkylsilylamides, alkylamines, alkylenediamines, cycloalkylamines (N-alkylated where appropriate and unsaturated where appropriate), basic heterocycles, ammonium hydroxides and carbocyclic amines. Examples are: sodium hydroxide, hydride, amide, methanolate, acetate, and carbonate, potassium tert-butanolate, hydroxide, carbonate, hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,5-diazabicyclo[5.4.0]undec-5-ene (DBU). Alkali and alkaline earth carbonates are preferred, especially potassium carbonate.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, typically benzene, toluene, xylene, mesitylene, tetraline, chlorobenzene, dichlorobenzene, bromobenzene, petroleum ether, hexane, cyclohexane, dichloromethane, chloroform, tetrachloromethane, dichloroethane, trichloroethene or tetrachloroethene; esters, such as ethyl acetate; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether (dimethoxyethane), dimethoxydiethyl ether, tetrahydrofuran or dioxan; ketones, such as acetone, methyl ethyl ketone or methyl isobutyl ketone; alcohols, such as methanol, ethanol, propanol, isopropanol, butanol, ethylene glycol or glycerol; amides, such as N,N-dimethylformamide, N,N-diethylformamide, N,N-dimethylacetamide, N-methylpyrrolidone or hexamethylphosphoric acid triamide; nitrites, such as acetonitrile or propionitrile; and sulfoxides, such as dimethyl sulfoxide. If the reaction takes place in the presence of a base, then bases used in excess, such as triethylamine, pyridine, N-methylmorpholine, or N,N-diethylaniline, can also serve as solvents or diluents. Preferred solvents are water-miscible ethers and water, especially mixtures thereof, in particular ethylene glycol dimethyl ether+$H_2O$+tetrahydrofuran.

The reaction is advantageously carried out within a temperature range of about 40° C. to about 180° C., preferably from about 60° C. to about 120° C., in many cases in the range between ambient temperature and the reflux temperature of the reaction mixture and preferably at normal pressure.

The reaction can take place without an inert gas atmosphere; however, it is preferably carried out under such an atmosphere, e.g. under nitrogen or argon, especially nitrogen.

The reaction time is not critical; a reaction time of about 0.1 to about 24 hours is preferred, especially about 0.5 to about 10 hours.

The isolation of the product takes place according to usual methods, e.g. by filtration, crystallization, distillation, or chromatography, or any suitable combination of these methods.

Especially preferred conditions for the reaction are described in Example H1-5.

Variant b):

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, typically benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxan; and sulfoxides, such as dimethyl sulfoxide.

The reaction is advantageously carried out within a temperature range of about 0° C. to about +120° C., preferably 80° C. to about +120° C. and preferably at normal pressure.

The reaction can take place without an inert gas atmosphere; however, it is preferably carried out under such an atmosphere, e.g. under nitrogen or argon, especially nitrogen.

The reaction time of about 1 to about 24 hours is preferred, especially about 12 to about 24 hours.

The isolation of the product takes place according to usual methods, e.g. by filtration, crystallization, distillation or chromatography or any suitable combination of these methods.

Advantageous method conditions are described in Example H2.

Salts of compounds of formula (I) may be prepared in a known manner. Acid addition salts, for example, are obtainable from compounds of formula (I) by treating with a suitable acid or a suitable ion exchange reagent and salts with bases are obtainable by treating with a suitable base or a suitable ion exchange reagent.

Salts of compounds of formula (I) can be converted into the free compounds of formula (I) by the usual means, acid addition salts e.g. by treating with a suitable basic composition or with a suitable ion exchange reagent, and salts with bases e.g. by treating with a suitable acid or a suitable ion exchange reagent.

Salts of compounds of formula (I) can be converted into other salts of compounds of formula (I) in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds of formula (I) with salt-forming characteristics can be obtained in free form or in the form of salts.

The compounds of formula (I) may be present in the form of one of the possible isomers or as a mixture thereof, or as pure isomers or isomer mixtures, i.e. as a racemic mixture; the invention relates both to the pure isomers and to the racemic mixtures, and is hereinbefore and hereinafter understood as doing so, even if stereochemical details are not specifically mentioned in every case.

Resolution of the racemates can be achieved by known methods, for example by recrystallization from an optically active solvent, by chromatography on chiral adsorbants, e.g. high-pressure liquid chromatography (HPLC) on acetyl cellulose, by the use of suitable microorganisms, by cleavage with specific immobilized enzymes, through the formation of inclusion compounds, e.g. using chiral crown ether, wherein only one isomer is complexed.

According to the invention, apart from ilsolation of corresponding isomer mixtures, generally known methods of enantioselective synthesis can also be applied to obtain pure optical isomers, e.g. by carrying out the method of the invention using educts with correspondingly suitable stereochemistry.

It is of advantage to isolate or synthesize the biologically more active isomer in each case, if the individual components show differences in biological efficacy.

Compounds of formula (I) can also be obtained in the form of their hydrates and/or also can include other solvents, used for example where necessary for the crystallization of compounds present in solid form.

The invention relates to all those forms of the method, according to which one starts from a compound obtainable as a primary material or an intermediate at any stage of the method and carries out all or some of the missing steps or uses, or especially under the reaction conditions produces, a starting material in the form of a derivative or a salt and/or its racemate or enantiomer.

In the method of the present invention, the starting materials and intermediates used are preferably those that lead to the compounds of formula (I) described at the beginning as being especially useful.

The invention relates especially to the method of preparation described in Example H1.

Methods for the preparation of compounds of formula (II) and of the requisite precursors are familiar to persons skilled in the art. In particular, a method for preparing compounds of the formula (II) type from a compound of formula (III)

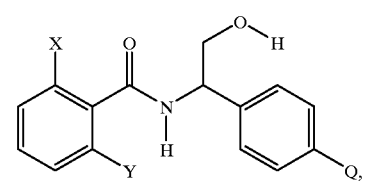

wherein X, Y and Q have the same meanings as defined for formula (II), is described for example in Chem. Rev. (1971), 71, 483–505.

A method for preparing a compound of formula (III) from a compound of formula (IV)

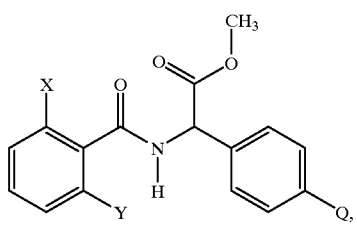

wherein X, Y and Q have the same meanings as defined for formula (II), is described for example in Hudlicky, Reductions in Organic Chemistry (1984), 136.

A method for preparing a compound of formula (IV) from a compound of formula (V)

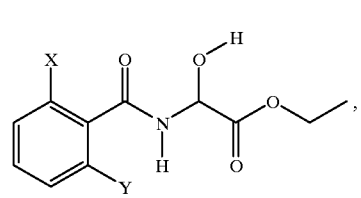

wherein X, Y and Q have the same meanings as defined for formula (II), is described for example in Synthesis (1984), 85–110. A method for preparing compounds of formula (V) is known from Tetrahedron (1975) 31, 863–866, and Tetrahedron (1977) 33, 881–883.

A further object of the invention is a compound of formula (II)

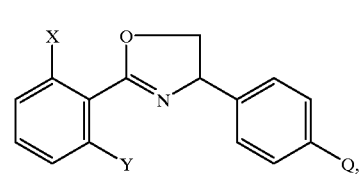

wherein X and Y are, independently of one another, fluorine or chlorine, and
Q is bromine or iodine.

The compounds of formula (I) according to the invention are active substances for use in pest control offering very favourable biocidal efficacy and a very broad spectrum of activity of preventive and/or curative merit with favourable tolerability in warm-blooded animals, fish, and plants even at low concentrations. Surprisingly, they are equally suitable for the control of crop-damaging parasites, of ectoparasites and endoparasites in humans, and above all in livestock, domestic animals and pets. They are active against all or individual development stages of animal pests showing normal sensitivity, as well as those showing resistance, such as insects and members of the order acarina, molluscs such as representatives of the class Gastropoda; nematodes, cestodes and trematodes. The active ingredients according to the invention are active against all or individual development stages of animal pests showing normal sensitivity, as well as those showing resistance, such as insects and members of the order acarina. The insecticidal or acaricidal effect of the active substances of the invention can manifest itself directly, i.e. killing the pests either immediately or after some time has elapsed, for example when moulting occurs, or indirectly, e.g. reducing the number of eggs laid and/or the hatching rate, good efficacy corresponding to a pesticidal rate (mortality) of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Lepidoptera and Coleoptera. Very especially good control is possible of the following families, genuses and species of pests:

Abagrotis spp., Abraxas spp., Acantholeucania spp., Acanthoplusia spp., Acarus spp., *Acarus siro,* Aceria spp., *Aceria sheldoni,* Acieris spp., Acoloithus spp., Acompsia spp., Acossus spp., Acria spp., Acrobasis spp., Acrocercops spp., Acrolepia spp., Acrolepiopsis spp., Acronicta spp., Acropolitis spp., Actebia spp., Aculus spp., *Aculus schlechtendali,* Adoxophyes spp., *Adoxophyes reticulana,* Aedes spp., *Aedes aegypti,* Aegeria spp., Aethes spp., Agapeta spp., Agonopterix spp., Agriopis spp., Agriotes spp., Agriphiia spp., Agrochola spp., Agroperina spp., Alabama spp., *Alabama argillaceae,* Agrotis spp., Albuna spp., Alcathoe spp., Alcis spp., Aleimma spp., Aletia spp., Aleurothrixus spp., *Aleurothrixus floccosus,* Aleyrodes spp., *Aleyrodes brassicae,* Allophyes spp., Alsophila spp., Amata spp., Amathes spp., Amblyomma spp., Amblyptilia spp., Ammoconia spp., Amorbia spp., Amphion spp., Amphipoea spp., Amphipyra spp., Amyelois spp., Anacamptodes spp., Anagrapha spp., Anarsia spp., Anatrychyntis spp., Anavitrinella spp., Ancylis spp., Andropolia spp., Anhimella spp., Anobiidae, *Anobium punctatum,* Antheraea spp., Antherigona spp., *Antherigona soccata,* Anthonomus spp., *Anthonomus grandis,* Anticarsia spp., *Anticarsia gemmatalis,* Aonidiella spp., Apamea spp., Aphania spp., Aphelia spp., Aphididae, Aphis spp., *Aphis pomi, A. craccivora, A. gossypiella,* Apidae, Apotomis spp., Aproaerema spp., Archippus spp., Archips spp., Acromyrmex, Arctia spp., Argas spp., Argolamprotes spp., Argyresthia spp., Argyrogramma spp., Argyroploce spp., Argyrotaenia spp., Arotrophora spp., Ascotis spp., Aspidiotus spp., Aspilapteryx spp., Asthenoptycha spp., Aterpia spp., Athetis spp., Atomaria spp., *Atomaria linearis,* Atta spp., Atypha spp., Autographa spp., Axylia spp., Bactra spp., Barbara spp., Batrachedra spp., Battaristis spp., Bembecia spp., Bemisia spp., *Bemisia tabaci,* Bibio spp., *Bibio hortulans,* Bisigna spp., Blastesthia spp., Blatta spp., Blatella spp., *Blattella germanica,* Blepharosis spp., Bleptina spp., Boarmia spp., Bombyx spp., Bomotocha spp., Boophilus spp., Bovicola spp., Brachmia spp., Bradina spp., Brevipalpus spp., Brithys spp., Bryobia spp., *Bryobia praetiosa,* Bryotropha spp., Bupalus spp., Busseola spp., *Busseola fusca,* Cabera spp., Cacoecimorpha spp., Cadra spp., *Cadra cautella,* Caenurgina spp., Calipitrimerus spp., Callierges spp., Calliphora spp., *Calliphora erythrocephala,* Calophasia spp., Caloptiiia spp., Calybites spp., Capnoptycha spp., Capua spp., Caradrina spp., Caripeta spp., Carmenta spp., Carposina spp., *Carposina nipponensis,* Catamacta spp., Catelaphris spp., Catoptria spp., Caustoloma spp., Celaena spp., Celypha spp., Cenopis spp., Cephus spp., Ceramica spp., Cerapteryx spp., Ceratitis spp, Ceratophyllus spp., Ceropiaster spp., Chaetocnema spp., *Chaetocnema tibialis,* Chamaesphecia spp., Charanvca spp., Cheimophila spp., Chersotis spp., Chiasmia spp., Chilo spp., Chionodes spp., Chorioptes spp., Choristoneura spp., Chrysaspidia spp., Chrysodeixis spp., Chrysomyla spp., Chrysomphalus spp., *Chrysomphalus dictyospermi, Chrysomphalus aonidium,* Chrysoteuchia spp., Cilix spp., Cimex spp., Clysia spp., *Clysia ambiguella,* Clepsis spp., Cnaemidophorus spp., Cnaphalocrocis spp., Cnephasia spp., Coccus spp., *Coccus hesperidum,* Cochylis spp., Coleophora spp., Colotois spp., Commophila spp., Conistra spp., Conopomorpha spp., Corcyra spp., Cornutiplusia spp., Cosmia spp., Cosmopolites spp., Cosmopterix spp., Cossus spp., Costaeonvexa spp., Crambus spp., Creatonotos spp., Crocidolomia spp., *Crocidolomia binotalis,* Croesia spp., Crymodes spp., Cryptaspasma spp., Cryptoblabes spp., Cryptocala spp., Cryptophlebia spp., *Cryptophlebia leucotreta,* Cryptoptila spp., *Ctenocephalides felis, Ctenocephalides canis,* Ctenopseustis spp., Cucullia spp., Curculio spp., Culex spp., Cuterebra spp., Cydia spp., *Cydia pomonella,* Cymbalophora spp., Dactylethra spp., Dacus spp., Dadica spp., Damalinea spp., Dasychira spp., Decadarchis spp., Decodes spp., Deilephila spp., Deltodes spp., Dendrolimus spp., Depressaria spp., Dermacentor spp., Dermatobia spp., Dermatophagoides spp., Dermestes spp., Dermanyssus spp., *Dermanyssus gallinae,* Diabrotica spp., *D. balteata,* Diachrysia spp., Diaphania spp., Diarsia spp., Diasemia spp., Diatraea spp., Diceratura spp., Dichomeris spp., Dichrocrocis spp., Dichrorampha spp., Dicycla spp., Dioryctria spp., Diparopsis spp., *Diparopsis castanea,* Dipieurina spp., Diprion spp., Diprionidae, Discestra spp., Distantielia spp., *Distantiella theobroma,* Ditula spp., Diurnea spp., Doratopteryx spp., Drepana spp., Drosphila spp., *Drosphila melanogaster,* Dysauxes spp., Dysdercus spp., Dysstroma spp., Eana spp., Earias spp., Ecclitica spp., Ecdytolopha spp., Ecpyrrhorrhoe spp., Ectomyelois spp., Eetropis spp., Egira spp., Elasmopalpus spp., Emmelia spp., Empoasca spp., Empyreuma spp., Enargia spp., Enarmonia spp., Endopiza spp., Endothenia spp., Endotricha spp., Eoreuma spp., Eotetranychus spp., *Eotetranychus carpini,* Epagoge spp., Epelis spp., Epilachna spp., Ephestia spp., *Ephestia kuehniella,* Ephestiodes spp., Epiblema spp., Epiehoristodes spp., Epinotia spp., Epiphyas spp., Epiplema spp., Epipsestis spp., Epirrhoe spp., Episimus spp., Epitymbia spp., Eptlachna spp., Erannis spp., Erastria spp., Eremnus spp., Ereunetis spp., Eriophyes spp., Eriosoma spp., *Eriosoma lanigerum,* Erythroneura spp., Estigmene spp., Ethmia spp., Etiella spp., Euagrotis spp., Eucosma spp., Euehlaena spp., Euelidia spp., Eueosma spp., Euchistus spp., Eucosmomorpha spp., Eudonia spp., Eufidonia spp., Euhyponomeutoides spp., Eulepitodes spp., Euila spp., Eulithis spp., Eupithecia spp., Euplexia spp., Eupoecilia spp., *Eupoecilia ambiguella,* Euproctis spp., Eupsilia spp., Eurhodope spp., Eurois spp., Eurygaster spp., Eurythmia spp., Eustrotia spp., Euxoa spp., Euzophera spp., Evergestis spp., Evippe spp., Exartema spp., Fannia spp., Faronta spp., Feltia spp., Filatima spp., Fishia spp., Frankliniella spp., Fumibotys spp., Gaesa spp., Gasgardia spp., Gastrophilus spp., Gelechia spp., Gilpinia spp., *Gilpinia polytoma,* Glossina spp., Glyphipterix spp., Glyphodes spp., Gnorimoschemini spp., Gonodonta spp., Gortyna spp., Gracillaria spp., Graphania spp., Grapholita spp., Grapholitha spp., Gravitarmata spp., Gretchena spp., Griselda spp., Gryllotalpa spp., Gynaephora spp., Gypsonoma spp., Hada spp., Haemaphysalis spp., Haematopinus spp., Halisidota spp., Harpipteryx spp., Harrisina spp., Hedya spp., Helicoverpa spp., Heliophobus spp., Heliothis spp., *Heliothis virescens,* Hellula spp., *Hellula undalis,* Helotropa spp., Hemaris spp., Hercinothrips spp., Herculia spp., Hermonassa spp., Heterogenea spp., Hodotermitidae, Holomelina spp., Homadaula spp., Homoeosoma spp., Homoglaea spp., Homohadena spp., Homona spp., Homonopsis spp., Hoplocampa spp., Hoplodrina spp., Hoshinoa spp., Hyalomma spp., Hydraecia spp., Hydriomena spp., Hyles spp., Hyloicus spp., Hypagyrtis spp., Hypatima spp., Hyphantria spp., *Hyphantria cunea,* Hypocala spp., Hypocoena spp., Hypoderma spp., Hypobosca spp., Hypsipyla spp., Hyssia spp., Hysterosia spp., Idaea spp., Idia spp., Ipimorpha spp., Isia spp., Isochorista spp., Isophrictis spp., isopolia spp., Isotrias spp., Ixodes spp., Itame spp., Jodia spp., Jodis spp., Kalotermitidae, Kawabea spp., Keiferia spp., *Keiferia lycopersicella,* Labdia spp., Lacinipolia spp., Lambdina spp., Lamprothritpa spp., Laodelphax spp., Lasius spp., Laspeyresia spp., Leptinotarsa spp., *Leptinotarsa decemlineata,* Leptocorisa spp., Leptostales spp., Lecanium spp., *Lecanium cornii,* Lepidosaphes spp., Lepisma spp., *Lepisma saccharina,* Lesmone spp., Leucania spp., Leucinodes spp., Leucophaea spp., *Leucophaea maderae,* Leucoptera spp., *Leucoptera scitella,* Linognathus spp., Liposcelis spp., Liriomyza spp., Lissorhoptrus spp., Lithacodia spp., Lithocolletis spp., Lithomoia spp., Lithophane spp., Lixodessa spp., Lobesia spp., *Lobesia botrana,* Lobophora spp., Locusta spp., Lomanaltes spp., Lomographa spp., Loxagrotis spp., Loxostege spp., Lucilia spp., *Lucilia cuprina,* Lyctidae, Lymantria spp., Lymnaecia spp., Lyonetia spp., Lyriomyza spp., Macdonnoughia spp., Macrauzata spp., Macronoctua spp., Macrosiphus spp., Malacosoma spp., Maliarpha spp., Mamestra spp., *Mamestra brassicae,* Manduca spp., Manduca sexta, Marasmia spp., Margaritia spp., Matratinea spp., Matsumuraeses spp., Melanagromyza spp., Melipotes spp., Melissopus spp., Melittia spp., Melolontha spp., Meristis spp., Meritastis spp., Merophyas spp., Mesapamea spp., Mesogona spp., Mesoleuca spp., Metanema spp., Metendothenia spp., Metzneria spp., Micardia spp., Microcorses spp., Microleon spp., Mnesictena spp., Mocis spp., Monima spp., Monochroa spp., Monomorium spp., *Monomorium pharaonis,* Monopsis spp., Morrisonia spp., Musca spp., Mutuuraia spp., Myeiois spp., Myobia spp., Myocoptes spp., Mythimna spp., Myzus spp., *Myzus persicae,* Naranga spp., Nedra spp., Nemapogon spp., Neodiprion spp., Neosphaieroptera spp., Nephelodes spp., Nephotettix spp., *Nephotettix cincticeps,* Nezara spp., Nilaparvata spp., *Nilaparvata lugens,* Niphonympha spp., Nippoptiiia spp., Noctua spp., Nola spp., Notocelia spp., Notodonta spp., Nudaurelia spp., Ochropieura spp., Ocnerostoma spp., Oestrus spp., Olethreutes spp., Oligia spp., Olindia spp., Olygonychus spp., *Olygonychus gallinae,* Oncocnemis spp., Operophtera spp., Ophisma spp., Opogona spp., Oraesia spp., Ornithodorus spp., Orgyia spp., Oria spp., Orseolia spp., Orthodes spp., Orthogonia spp., Orthosia spp., Oryzaephilus spp., Oscinella spp., *Oscinella frit,* Osminia spp., Ostrinia spp., *Ostrinia nubilalis,* Otiorhynchus spp., Ourapteryx spp., Pachetra spp., Pachysphinx spp., Pagyda spp., Paleacrita spp., Paliga spp., Paithis spp., Pammene spp., Pandemis spp., Panemeria spp., Panolis spp., *Panolis flammea,* Panonychus spp., *Panonychus ulmi,* Parargyresthia spp., Paradiarsia spp., Paralobesia spp., Paranthrene spp., Parapandemis spp., Parapediasia spp., Parastichtis spp., Parasyndemis spp., Paratoria spp., Pareromeme spp., Pectinophora spp., *Pectinophora gossypiella,* Pediculus spp., Pegomyia spp., *Pegomyia hyoscyami,* Pelochrista spp., Pennisetia spp., Penstemonia spp., Pemphigus spp., Peribatodes spp., Peridroma spp., Perileucoptera spp., Periplaneta spp., Perizoma spp., Petrova spp., Pexicopia spp., Phalonia spp., Phalonidia spp., Phaneta spp., Phlyctaenia spp., Phlyctinus spp., Phorbia spp., Phragmatobia spp., Phricanthes spp., Phthorimaea spp., *Phthorimaea operculella,* Phyllocnistis spp., Phyllocoptruta spp., *Phyllocoptruta oteivora,* Phyllonorycter spp., Phyllophila spp., Phylloxera spp., Pieris spp., *Pieris rapae,* Piesma spp., Planococus spp., Planotortrix spp., Platyedra spp., Platynota spp., Platyptilia spp., Platysenta spp., Plodia spp., Plusia spp., Plutelia spp., *Plutella xylostella,* Podosesia spp., Polia spp., Popillia spp., Polymixis spp., Polyphagotarsonemus spp., *Polyphagotarsonemus latus,* Prays spp., Prionoxystus spp., Probole spp., Proceras spp., Prochoerodes spp., Proeulia spp., Proschistis spp., Proselena spp., Proserpinus spp., Protagrotis spp., Proteoteras spp., Protobathra spp., Protoschinia spp., Pselnophorus spp., Pseudaletia spp., Pseudanthonomus spp., Pseudaternelia spp., Pseudaulacaspis spp., Pseudexentera spp., Pseudococus spp., Pseudohermenias spp., Pseudoplusia spp., Psorergates spp., Psoroptes spp., Psylla spp., Psylliodes spp., Pterophorus spp., Ptycholoma spp., Pulex spp., Pulvinaria spp., *Pulvinaria aethiopica,* Pyralis spp., Pyrausta spp., Pyrgotis spp., Pyrreferra spp., Pyrrharctia spp., Quadraspidiotus spp., Rancora spp., Raphia spp., Reticulitermes spp., Retinia spp., Rhagoletis spp, *Rhagoletis pomonella,* Rhinotermitidae, Rhipicephalus spp., Rhizoglyphus spp., Rhizopertha spp., Rhodnius spp., Rhopalosiphum spp., Rhopobota spp., Rhyacia spp., Rhyacionia spp., Rhynchopacha spp., Rhyzosthenes spp., Rivula spp., Rondotia spp., Rusidrina spp., Rynchagiaea spp., Sabulodes spp., Sahlbergella spp., *Sahlbergella singularis,* Saissetia spp., Samia spp., Sannina spp., Sanninoidea spp., Saphoideus spp., Sarcoptes spp., Sathrobrota spp., Scarabeidae, Sceliodes spp., Schinia spp., Schistocerca spp., Schizaphis spp., Schizura spp., Schreckensteinia spp., Sciara spp., Scirpophaga spp., *Scirtothrips aurantii,* Scoparia spp., Scopula spp., Scotia spp., Scotinophara spp., Scotogramma spp., Scrobipalpa spp., Scrobipalpopsis spp., Semiothisa spp., Sereda spp., Sesamia spp., Sesia spp., Sicya spp., Sideridis spp., Simyra spp., Sineugraphe spp., Sitochroa spp., Sitobion spp., Sitophilus spp., Sitotroga spp., Solenopsis spp., Smerinthus spp., Sophronia spp., Spaelotis spp., Spargaloma spp., Sparganothis spp., Spatalistis spp., Sperchia spp., Sphecia spp., Sphinx spp., Spilonota spp., Spodoptera spp., *Spodoptera littoralis,* Stagmatophora spp., Staphylinochrous spp., Stathmopoda spp., Stenodes spp., Sterrha spp., Stomoxys spp., Strophedra spp., Sunira spp., Sutyna spp., Swammerdamia spp., Syllomatia spp., Sympistis spp., Synanthedon spp., Synaxis spp., Syncopacma spp., Syndemis spp., Syngrapha spp., Synthomeida spp., Tabanus spp., Taeniarchis spp., Taeniothrips spp., Tannia spp., Tarsonemus spp., Tegulifera spp., Tehama spp., Teleiodes spp., Telorta spp., Tenebrio spp., *Tenebrio molitor,* Tephrina spp., Teratoglaea spp., Termitidae, Terricula spp., Tethea spp., Tetranychus spp., *Tetranychus ulmi,* Thalpophila spp., Thaumetopoea spp., Thiodia spp., Thrips spp., *Thrips palmi, Thrips tabaci,* Thyridopteryx spp., Thyris spp., Tineola spp., Tipula spp., Tortricidia spp., Tortrix spp., Trachea spp., Trialeurodes spp., *Trialeurodes vaporariorum,* Triatoma spp., Triaxomera spp., Tribolium spp., Trichodectes spp., Trichoplusia spp., *Trichoplusia ni,* Trichoptilus spp., Trioza spp., *Trioza erytreae,* Triphaenia spp., Triphosa spp., Trogoderma spp., Tyria spp., Udea spp., Unaspis spp., *Unaspis citri,* Utetheisa spp., Valeriodes spp., Vespa spp., Vespamima spp., Vitacea spp., Vitula spp., Witlesia spp., Xanthia spp., Xanthorhoe spp., Xanthotype spp., Xenomicta spp., Xenopsylla spp., *Xenopsylla cheopsis,* Xestia spp., Xylena spp., *Xylocopa virginica,* Xylomyges spp., Xyrosaris spp., Yponomeuta spp., Ypsolopha spp., Zale spp., Zanclognathus spp., Zeiraphera spp., Zenodoxus spp., Zeuzera spp., Zygaena spp.;

from the class of the nematodes, for example, the families Filariidae and Setariidae and the genera Haemonchus, Trichostrongylus, Ostertagia, Nematodirus, Cooperia, Ascaris, Bunostumum, Oesophagostonum, Chabertia, Trichuris, especially *Trichuris vulpis,* Strongylus, Trichonema, Dictyocautus, Capillaria, Strongyloides, Heterakis, Toxocara, insbesondere Toxocara canis, Ascaridia, Oxyuris, Ancylostoma, especially *Ancylostoma caninum,* Uncinaria, Toxascaris and Parascaris; Dirofilaria, especially *Dirofilaria immitis* (heartworm); from the phylum of the molluscs especially representatives of the class Gastropoda; particularly the following families, genuses and species: Ampullariidae; Arion (*A. ater, A. circumscriptus, A. hortensis, A. rufus*); Bradybaenidae (*Bradybaena fruticum*); Cepaea (*C. hortensis, C. Nemoralis*); Cochiodina; Deroceras (*D. agrestis, D. empiricorum, D. laeve, D. reticulatum*); Discus (*D. rotundatus*); Euomphalia; Galba (*G. trunculata*); Helicella (*H. itala, H. obvia*); Helicidae (*Helicigona arbustorum*); Helicodiscus; Helix (*H. aspersa*); Limax (*L. cinereoniger, L. flavus, L. marginatus, L. maximus, L. tenellus*); Lymnaea; Milax (*M. gagates, M. marginatus, M. sowerbyi*); Opeas; Pomacea (*P. canaticulata*); Vallonia und Zanitoides.

The lifecycles of various parasites which can infest humans or animals are known to be very complex, which makes it extremely difficult to control the parasites. Ticks for example may feed exclusively from a single host or from several. They attach themselves to the host animal and feed off its blood. The females, when engorged, drop from the host animal and then lay a large number of eggs in a protected site of the surrounding environment. The developing larvae look for a new host animal, where they develop via the nymphal stage into adults, which in turn take a blood meal until engorged. Certain species feed on two and some on three hosts during their lifecycle.

Ticks of economic importance are above all those which belong to the species Amblyomma, Boophilus, Hyalomma, Ixodes, Rhipicephalus and Dermacentor, especially the species *Boophilus microplus* and *B. annulatus,* and most especially *B. microplus.* They are responsible for the transmission of numerous diseases which can affect humans and animals. The diseases which are mostly transmitted are bacterial, protozoan, rickettsial and viral. The pathogens of such diseases are transmitted especially by ticks which feed on more than one host. These diseases can lead to the debilitation or even death of the host animals. In most cases they cause considerable economic damage, for example by diminishing the value of meat from livestock, damaging the usable skin, or reducing milk production.

Ticks of the above species are usually controlled by treating the infested animals with an acaricidally active composition depending on the type of infestation involved, i.e. by curative means. The occurrence of ticks, for example on pasture land, is heavily dependent, however, on seasonal weather conditions, and the infestation of the host animals itself depends also on their resistance to the ticks. This means that the preventive control of ticks is difficult and time-consuming, because it is difficult to estimate the degree of infestation by the parasites and the resistance of the animals to them. Furthermore, when attempting the preventive control of parasites, lengthy surveillance for possible infestation is necessary, which creates additional problems. Curative control of the parasites is not usually the primary aim because, at the time when the control begins to work, considerable damage has often already occurred.

Owing to the equally complex lifecycle of fleas, none of the known methods for controlling these parasites is entirely satisfactory, in particular because most of the known control methods focus on applying the active ingredient to the habitat in the flea's various development stages. This method is very complex and often unreliable, however, because of the different development stages which a flea goes through and which respond quite differently to different classes of substance.

The flea infestation of animals, in particular of dogs and cats, is accompanied by unpleasant effects not only for the animal being treated, but also for the animal keeper. These untoward effects can result in e.g. local irritation, troublesome pruritus, or even allergies, and often lead to intense scratching. Moreover, animals infested with fleas are constantly exposed to the risk of becoming infected with Dipylidium spp. (i.e. tapeworms, cestodes), which are transmitted by fleas.

Surprisingly, it has now been found that certain forms of application, for example topical application, but especially systemic administration of the compounds of formula (I), where appropriate with the addition of one or more compounds from other substance classes, e.g. methoprene, hydroprene, dicyclanil and cythioate, or their salts, to potentiate the effect, can eliminate the said ectoparasites very rapidly and completely, thus intervening to block the complex development cycle of the parasites, and at the same time achieving an efficient control of the endoparasites. These compositions are even capable of exerting their excellent parasiticidal effect in full when given to the host animal systemically, i.e. orally, parenterally, subcutaneously, intramuscularly or intravenously. It is now possible, through selective periodic administration of these compounds, to break the cycle of constant reinfestation of the host animals with the various parasites in a simple manner and to achieve a lasting eradication of the parasites. The parasites are either killed or prevented from reproducing, or the juvenile stages are prevented from developing and are no longer able to harm the host animal.

A further preferred object of the present invention is thus a method for the control of parasites in and on humans, domestic animals, livestock and pets, comprising a composition which contains at least one compound of formula (I), or a veterinarily acceptable salt thereof, and is administered to the host animal orally, parenterally or by implant at a parasiticidally effective dose.

Essential to the invention is the fact that the composition of the invention is administered in such a way that the active ingredients which the composition comprises can be taken up in sufficient quantity with the blood of the host animal by endoparasites, ectoparasites and other parasites which can be regarded as vectors for the transmission of endoparasites, so that the eggs laid by the adult parasites and/or the larvae hatching therefrom are not able to develop.

This is achieved with the composition of the invention using different forms of application, e.g. through the oral administration of the composition comprising the active ingredients. Formulation in this case means e.g. presentation in the form of a powder, a tablet, granules, a capsule, an emulsion, a foam, or in a microencapsulated form, etc., although it is not absolutely necessary for the preparation to be given directly to the animal—it can also be added to the animal's feed where expedient. Of course, all compositions to be given by the oral route may contain, along with the usual formulation assistants, further additives designed to encourage their uptake by the host animal, e.g. appropriate aromas and flavours. Because of its simplicity of application, the oral route of administration is one of the preferred objects of this invention. A further form of administration is the parenteral route, e.g. by subcutaneous or intravenous injection, topical application, long-term implantation (depot), or an injection of microcapsules (so-called microspheres).

Oral administration includes e.g. giving animal feed, for example dog or cat food, in which the active ingredients are already mixed, e.g. in the form of biscuits, chewable tablets, water-soluble capsules or tablets, in a water-soluble form that can be applied in drops onto the feed or in other forms that are miscible with the animal feed. Implants include all devices which can be inserted into the body of the animal for delivery of the substance.

Percutaneous forms of administration include for example subcutaneous, dermal, intramuscular and even intravenous administration of injectable forms. Apart from the usual injection syringes with needles, needleless systems and pour-on and spot-on formulations may also be expedient.

Through the selection of a suitable formulation, it is possible to promote the permeability of the active ingredients through the living tissue of the animal and maintain their availability. This is of importance if, for example, one or more poorly soluble active ingredients are used whose solubility needs to be promoted because the body fluid of the animal is only able to dissolve small quantities of the active ingredients at any one time.

Furthermore, the active ingredients may also be present in a matrix formulation, which physically prevents their decomposition and maintains the availability of the active ingredients. This matrix formulation is injected into the body and remains there as a form of depot from which the active ingredients are continuously released. Such matrix formulations are known to persons skilled in the art. They are generally waxlike, semisolid excipients, such as e.g. vegetable waxes and polyethylene glycols of high molecular weight or copolymers from degradable polyesters.

A high bioavailability of the active ingredients is also obtained by inserting an implant of the active ingredients into the animal. Such implants are widespread in veterinary medicine and often consist of silicon-containing rubber. In these implants, the active ingredients are dispersed in the solid rubber or are located inside a hollow rubber body. It should be noted that active ingredients are selected which are soluble in the rubber implant, because they are dissolved first in the rubber and then continuously released from the rubber material into the body fluid of the animal being treated.

The rate at which the active ingredients are released from the implant and thus the time during which the implant exerts an effect are generally determined by the accuracy with which the implant is calibrated (quantity of active ingredient in the implant), the environment of the implant, and the formulation of the polymer from which the implant is made.

The delivery of active ingredients using an implant is a further preferred object of the present invention. Administration of this kind is extremely economical and effective because an implant of the correct dimensions ensures a constant concentration of the active substances in the tissue of the host animal. Implants today can be designed and implanted in such a way that they are capable of delivering the active ingredients over a period of several months.

The mixing of veterinary adjuvants with animal feed is well-known in the field of animal health. Usually a so-called premix is first prepared, in which the active ingredients are dispersed in a liquid or finely distributed in a solid carrier medium. This premix normally contains about 1 to 800 g of the substances per kg of premix depending on the desired final concentration in the feed.

It is known moreover that active ingredients can be hydrolysed or their effects attenuated by the constituents of the feed. These active substances are routinely formulated in a protective matrix, e.g. in gelatin, before being added to the premix.

The compounds of formula (I) are usefully administered in a dose from 0.01 to 800, preferably from 0.1 to 200, and especially from 0.5 to 50 mg/kg bodyweight with respect to the human subject and/or the host animal, oral administration being preferred.

A good dose of a compound of formula (I) which can be administered regularly to the host animal is especially 2.5–5 mg/kg bodyweight in the cat and 0.5–15 mg/kg per kg bodyweight in the dog. It is expedient to carry out the administration at regular intervals, e.g. every few days, weekly, or monthly.

The total dose can vary with the same active ingredient both between and within animal species, since the dose depends among other things on the weight and the constitution of the animal.

For the formulation of compositions that are to be administered to humans, domestic animals, livestock, and pets, the adjuvants known from veterinary practice for oral, parenteral and implant forms can be used. The following is a non-exhaustive list of some examples.

Suitable carriers are in particular fillers, such as sugars, e.g. lactose, saccharose, mannitol or sorbitol, cellulose preparations and/or calcium phosphates, e.g. tricalcium phosphate or calcium hydrogen phosphate, in a broader sense also binders, such as starch pastes using e.g. corn, wheat, rice or potato starch, gelatin, tragacanth, methyl cellulose and/or, if desired, disintegrants, such as the above-mentioned starches, in a broader sense also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Tablet cores may be provided with suitable, where appropriate enteric, coatings, using inter alia concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes, flavours or pigments may be added to the tablets or tablet coatings, for example for identification purposes or to indicate different doses of active ingredient.

Further orally administrable pharmaceutical compositions include hard capsules consisting of gelatin, and also soft, sealed capsules consisting of gelatin and a plasticizer, such as glycerol or sorbitol. The hard capsules may contain the active ingredient in the form of granules, for example in admixture with fillers, such as lactose, binders, such as starches, and/or glidants, such as talc or magnesium stearate, and where appropriate stabilizers. In soft capsules, the active ingredients are preferably dissolved or suspended in suitable liquids, such as fatty oils, paraffin oil, or liquid polyethylene glycols, and stabilizers may likewise be added. Amongst other forms, capsules which can be both easily chewed and also swallowed whole are preferred.

The formulations suitable for parenteral administration are especially aqueous solutions of the active ingredients in water-soluble form, e.g. water-soluble salts, in the broader sense also suspensions of the active ingredients, such as appropriate oily injectable suspensions using suitable lipophilic solvents or vehicles, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilizers.

The compositions of the invention can be prepared in a known manner, e.g. for example by means of conventional mixing, granulating, coating, dissolving or lyophilizing methods. Pharmaceutical compositions for oral administration can be obtained, for example, by combining the active ingredients with solid carriers, granulating a resulting mixture where appropriate, and processing the mixture or granules, if desired or necessary, to form tablets or tablet cores following the addition of suitable excipients.

The use of compounds of formula (I) according to the invention for the protection of plants against parasitic pests forms a particular focus of the present invention.

Pests of said type which occur on plants, especially on crops and ornamentals in agriculture, horticulture and forestry, or on parts of such plants, such as fruits, blooms, leaves, stems, tubers or roots, can be controlled, i.e. kept in check or eradicated, using the active ingredients of the invention, this protection remaining for parts of some plants whose growth does not occur until later.

Target crops within the scope of this application include especially cereals, such as wheat, barley, rye, oats, rice, corn or sorghum; beet, such as sugar beet or fodder beet; fruit, e.g. pomes, drupes and soft fruit, such as apples, pears, plums, peaches, almonds, cherries or berries, e.g. strawberries, raspberries or blackberries; leguminous plants, such as beans, lentils, peas or soybean; oleaginous fruits, such as rape, mustard, poppy, olives, sunflowers, coconut, castor oil plants, cocoa beans or groundnuts; cucumber plants, such as pumpkins, cucumbers or melons; fibrous plants, such as cotton, flax, hemp or jute; citrus fruits, such as oranges, lemons, grapefruit or mandarins; vegetables, such as spinach, lettuce, asparagus, cabbages, carrots, onions, tomatoes, potatoes or paprika; lauraceae, such as avocado, cinnamon or camphor; and tobacco, nuts, coffee, aubergines, sugar cane, tea, pepper, vines, hops, banana plants, natural rubber plants and ornamentals.

The active ingredients of the invention are especially suitable for controlling *Nila parvata lugens, Heliothis virescens, Spodoptera littoralis, Diabrotica balteata, Panonychus ulmi* and *Tetranychus urticae* in vegetable, fruit, and rice crops.

Other indication areas for the active ingredients of the invention are the protection of supplies and stores and of material, as well as in the hygiene sector, especially the protection of domestic animals and livestock against pests of said type.

The invention therefore relates also to pesticides, such as emulsifiable concentrates, suspension concentrates, directly sprayable or dilutable solutions, coatable pastes, dilute emulsions, spray powders, soluble powders, dispersible powders, wettable powders, dusts, granulates or encapsulated polymers (chosen in accordance with the intended objectives and prevailing circumstances), comprising at least one active ingredient of the invention.

The active ingredient is used in these compositions in pure form and a solid active ingredient e.g. in a specific particle size, or preferably together with—at least—one of the adjuvants conventionally employed in the art of formulation, such as extenders, e.g. solvents or solid carriers, or surface-active compounds (surfactants). For parasite control in humans, domestic animals, livestock, and pets of course only physiologically acceptable adjuvants are used.

In crop protection, suitable solvents include for example: aromatic hydrocarbons, partially hydrogenated where necessary, preferably fractions of alkylbenzenes having 8 to 12 carbon atoms, such as xylene mixtures, alkylated naphalthene or tetrahydronaphthalene, a liphatic or cycloaliphatic hydrocarbons, such as paraffins or cyclohexane, alcohols, such as ethanol, propanol or butanol, glycols and their ethers and esters, such as propylene glycol, dipropylene glycol ether, ethyl glycol or ethylene glycol monomethyl or ethyl ether, ketones, such as cyclohexanone, isophorone or diacetanol alcohol, strongly polar solvents, such as N-methylpyrrolid-2-one, dimethyl sulfoxide or N,N-dimethylformamide, water, vegetable oils epoxidized where appropriate, such as rape, castor, coconut, or soybean oil epoxidized where appropriate, and silicone oils.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite, and suitable non-sorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are non-ionic, cationic and/or anionic surfactants having good emulsifying, dispersing and wetting properties. The surfactants specified below are to be regarded only as examples; the relevant literature describes many other surfactants that are commonly used in formulation technology and are suitable according to the invention.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Suitable non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have as substituent at least one $C_8$–$C_{22}$ alkyl radical and, as further substituents, lower—where appropriate—halogenated alkyl, benzyl or lower hydroxyalkyl radicals. The salts are preferably in the form of halides, methylsulfates or ethylsulfates. Examples are stearyltrimethylammonium chloride and benzyldi(2-chloroethyl) ethylammonium bromide.

Suitable anionic surfactants can be both water-soluble soaps and water-soluble synthetic surfactant compounds. Suitable soaps are the alkali metal salts, alkaline earth metal salts or unsubstituted or substituted ammonium salts of higher fatty acids ($C_{10}$–$C_{22}$), for example the sodium or potassium salts of oleic or stearic acid, or of natural fatty acid mixtures which can be obtained for example from coconut oil or tallow oil; the fatty acid methyltaurin salts may also be used. More frequently, however, synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammoniums salts and have an 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

The compositions for use in crop protection and in humans, domestic animals, livestock, and pets usually contain 0.1 to 99%, especially 0.1 to 95%, of active ingredient and 1 to 99.9%, especially 5 to 99.9%,—at least—one solid or liquid adjuvant, usually 0 to 25%, especially 0.1 to 20%, of the composition comprising surfactants (% in each case means percent by weight). Whereas concentrated compositions are preferred as commercial product, the end consumer usually uses diluted compositions, which exhibit substantially lower concentrations of active ingredient.

The composition of preferred crop protection agents is especially as follows (%=percent by weight):

| Emulsifiable concentrates: | |
| --- | --- |
| Active ingredient: | 1 to 90%, preferably 5 to 20% |
| Surfactant: | 1 to 30%, preferably 10 to 20% |
| Solvent: | 5 to 98%, preferably 70 to 85% |
| Dusts: | |
| Active ingredient: | 0.1 to 10%, preferably 0,1 to 1% |
| Solid carrier: | 99.9 to 90%, preferably 99.9 to 99% |
| Suspension concentrates: | |
| Active ingredient: | 5 to 75%, preferably 10 to 50% |
| Water: | 94 to 24%, preferably 88 to 30% |
| Surfactant: | 1 to 40%, preferably 2 to 30% |
| Wettable powders: | |
| Active ingredient: | 1 to 90%, preferably 10 to 80% |
| Surfactant: | 1 to 20%, preferably 10 to 15% |
| Solid carrier: | 5 to 99%, preferably 15 to 98% |
| Granulates: | |
| Active ingredient: | 0.5 to 30%, preferably 3 to 15% |
| Solid carrier: | 99.5 to 70%, preferably 97 to 85% |

The activity of the crop protection agents of the invention can be substantially broadened and adapted to prevailing circumstances by adding other insecticidal substances. Additional active ingredients are, for example, substances from the following classes: organic phosphorus compounds, nitrophenols and their derivatives, formamidines, acylureas, carbamates, pyrethroids, nitroenamines and their derivatives, pyrroles, thioureas and their derivatives, chlorinated hydrocarbons and *Bacillus thuringiensis* preparations. The compositions of the invention can also contain further solid or liquid adjuvants, such as stabilizers, e.g. vegetable oils, epoxidized where appropriate (e.g. epoxidized coconut oil, rapeseed oil or soya oil), antifoaming agents, e.g. silicone oil, preservatives, viscosity modulators, binders and/or tackifiers, as well as fertilizers or other active ingredients to achieve specific effects, e.g. acaricides, bactericides, fungicides, nematocides, molluscicides or selective herbicides.

The crop protection agents of the invention are prepared in a known manner, in the absence of adjuvants e.g. by grinding, sieving, and/or compressing a solid active ingredient or active ingredient mixture, e.g. to a specific particle size, and in the presence of at least one adjuvant, e.g. by intimate mixing and/or grinding of the active ingredient or active ingredient mixture with the adjuvant(s). These methods for preparing compositions of the invention and the use of compounds of the formula (I) for preparing these compositions likewise form an object of the invention.

The methods of applying the crop protection agents, i.e. the methods for controlling pests of said type, such as spraying, atomizing, dusting, coating, dressing, scattering or pouring (chosen in accordance with the intended objectives and prevailing circumstances), and the use of the compositions for controlling pests of said type are further objects of the invention. Typical concentrations of active ingredient are between 0.1 and 1000 ppm, preferably between 0.1 and 500 ppm. The rates of application are generally 1 to 2000 g of active ingredient (a.i.) per hectare (ha=approximately 2.471 acres), especially 10 to 1000 g a.i./ha, and preferably 20 to 600 g a.i./ha.

A preferred method of application for crop protection is to apply the active ingredient to the leaves of the plant (leaf application), the number of applications and the rate of application depending on the intensity of infestation by the corresponding pathogen. However, the active ingredients can also penetrate the plant through the roots via the soil (systemic action) by impregnating the locus of the plant with a liquid composition, or by applying the compounds in solid form to the soil, e.g. in granular form (soil application). With lowland rice cultures, granulates may also be dosed into the flooded rice field.

The crop protection agents of the invention are also suitable for protecting vegetative reproductive material, e.g. seeds, such as fruits, tubers or grains, or plant seedlings, from animal pests. The reproductive material can be treated with the composition before the start of cultivation, seeds for example being dressed before they are sown. The active ingredients of the invention can also be applied to seeds (coating) by either soaking the seeds in a liquid composition or coating them with a solid composition. The composition can also be given when the reproductive material is introduced to the place of cultivation, e.g. when the seeds are sown in the seed furrow. The treatment procedures for vegetative reproductive material and the vegetative reproductive material thus treated are further objects of the invention.

In the following formulation examples of use in humans, domestic animals, livestock, and pets, the term "active ingredient" is understood to mean one or more active ingredients of formula (I) or a salt thereof, and preferably 2-(2,6-difluorophenyl)-4-(4'-trifluoromethylbiphenyl-4-yl)-4,5-dihydro-oxazole.

| Tablets: containing one of the active ingredients of formula (I) can be prepared as follows: | |
|---|---|
| Composition (for 1000 tablets) | |
| Active ingredient of formula (I) | 25 g |
| Lactose | 100.7 g |
| Wheat starch | 6.25 g |
| Polyethylene glycol 6000 | 5.0 g |
| Talc | 5.0 g |
| Magnesium stearate | 1.8 g |
| Deionized water | q.s. |

Preparation: All solid ingredients are first passed through a sieve with a mesh size of 0.6 mm. The active ingredient, the lactose, the talc, and half the starch are then mixed. The other half of the starch is suspended in 40 ml water, and this suspension is added to a boiling solution of the polyethylene glycol in 100 ml water. The resulting starch paste is added to the mixture, and this is then granulated, water being added where appropriate. The granulate is dried overnight at 35°, passed through a sieve with a mesh size of 1.2 mm, mixed with the magnesium stearate, and compressed to form tablets concave on both sides and with a diameter of 6 mm.

| Tablets: each containing a total of 0.0183 g active ingredient are prepared as follows: | |
|---|---|
| Composition (for 10,000 tablets) | |
| Active ingredient of formula (I) | 183.00 g |
| Lactose | 290.80 g |
| Potato starch | 274.70 g |
| Stearic acid | 10.00 g |
| Talc | 217.00 g |
| Magnesium stearate | 2.50 g |
| Colloidal silica | 32.00 g |
| Ethanol | q.s. |

A mixture of the active ingredient, the lactose and 274.70 g potato starch is wetted with an ethanolic solution of stearic acid and granulated through a sieve. After drying, the remaining potato starch, the talc, the magnesium stearate, and the colloidal silica are added and the mixture compressed to form tablets of 0.1 g each in weight, which—if so desired—can be scored to allow for a finer adjustment of the dose.

| Capsules: each containing a total of 0.022 g active ingredient can be prepared as follows: | |
|---|---|
| Composition (for 1000 capsules) | |
| Active ingredient of formula (I) | 22.00 g |
| Lactose | 249.80 g |
| Gelatin | 2.00 g |
| Corn starch | 10.00 g |
| Talc | 15.00 g |
| Water | q.s. |

The active ingredient is mixed with the lactose, the mixture wetted evenly with an aqueous solution of the gelatin and granulated through a sieve with a mesh size of 1.2–1.5 mm. The granulate is mixed with the dried corn starch and the talc, and portions of 300 mg are filled into hard gelatin capsules (size 1).

Premix (feed additive)

0.16 parts by weight of active ingredient 4.84 parts by weight of secondary calcium phosphate, alumina, aerosil, carbonate or calcium carbonate are mixed until homogeneous with 95 parts by weight of an animal feed or 0.41 parts by weight of active ingredient 5.00 parts by weight of aerosil/calcium carbonate (1:1) are mixed until homogeneous with 94.59 parts by weight of a commercially available feed.

| | Boli: | |
|---|---|---|
| I | Active ingredient | 33.00% |
| | Methylcellulose | 0.80% |
| | Silicic acid, highly dispersed | 0–80% |
| | Corn starch | 8.40% |
| II | Lactose, cryst. | 22.50% |
| | Corn starch | 17.00% |
| | Microcrist. cellulose | 16.50% |
| | Magnesium stearate | 1.00% |

The methylcellulose is first stirred into water. After the material has swollen, the silicic acid is stirred in and the mixture homogeneously suspended. The active ingredient and the corn starch are mixed. The aqueous suspension is worked into this mixture and kneaded to a dough. The resulting mass is granulated through a 12M sieve and dried. In a further step, all 4 adjuvants are thoroughly mixed. Finally, the premixtures resulting from the first two partial steps are mixed and compressed to form boli.

| | Injectables: | |
|---|---|---|
| A. | Oily vehicle (slow release) | |
| | Active ingredient | 0.1–1.0 g |
| | Groundnut oil | ad 100 ml |
| or | | |
| | Active ingredient | 0.1–1.0 g |
| | Sesame oil | ad 100 ml |

Preparation: The active ingredient is dissolved in part of the oil with stirring and where appropriate gentle heating, then made up to the desired volume and sterile-filtered through a suitable membrane filter with a pore size of 0.22 μm.

The following examples of preparation and application serve to explain the invention without limiting it to the individual aspects of these examples.

PREPARATIVE EXAMPLES

Example H1: Preparation of 2-(2,6-difluorophenyl)-4-(4'-trifluoromethylbiphenyl-4-yl)-4,5-dihydro-oxazole of the formula

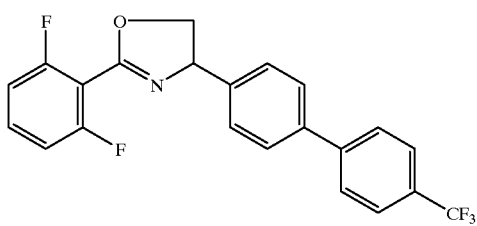

Example H1-1: (2,6-Difluorobenzoylamino)hydroxyacetic acid ethyl ester

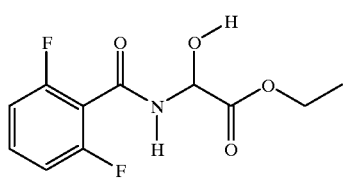

78.5 g (0.5 mol) 2,6-Difluorobenzamide is refluxed for 1 hour with 61.3 g (0.6 mol) ethyl glyoxylate in 400 ml toluene. After cooling to ambient temperature, the mixture is diluted with the same quantity of toluene and filtered off. The solid matter is washed with hexane and dried under a vacuum at 60° C. This yields the title compound with a melting point of 156-157° C.

Example H1-2: (2,6-Difluorobenzoylamino)-p-iodophenylacetic acid methyl ester

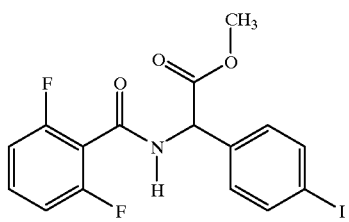

26 g (2,6-Difluorobenzoylamino)hydroxyacetic acid ethyl ester is stirred with 20.4 g iodobenzene in 120 ml sulfuric acid 98% for 24 hours at a temperature of about 35° C. The mixture is poured on ice and extracted 3 times with dichloromethane, dried and the solvent evaporated in a rotary evaporator. The residue is taken up in 200 ml methanol, 5 ml thionyl chloride is added, and the mixture is boiled for 2 hours under reflux. The solution is concentrated by evaporation and chromatographed on silica gel with ethyl acetate: hexane 1:3. The solution is evaporated and the residue recrystallized from toluene. This yields the title compound with a melting point of 155–156° C.

Example H1-3: 2,6-Difluoro-.N.-(2-hydroxy-1-[p-iodophenyl]ethyl)benzamide

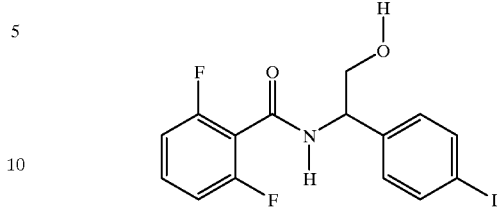

17g (2,6-Difluorobenzoylamino)-p-iodophenylacetic acid methyl ester is stirred for 1 hour under reflux in 200 ml ethanol with 1.5 g sodium borohydride. The mixture is concentrated by evaporation and the residue distributed between ethyl acetate and water. The organic phase is washed with water and brine, dried and concentrated by evaporation. Chromatography on silica gel with ethyl acetate: hexane, 2: 3, yields the title compound with a melting point of 153–155° C.

Example H1-4: 2-(2,6-Difluorophenyl)-4-iodophenyl-4,5-dihydro-oxazole

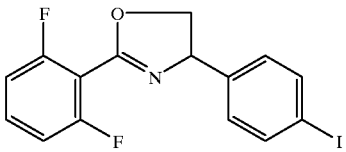

7.0 g (0.0174 mol) 2,6-Difluoro-.N.-(2-hydroxy-1-[p-iodophenyl]ethyl)benzamide is suspended in 20 ml toluene, 2.9 ml thionylchloride is added, and this is refluxed for 45 minutes. The mixture is concentrated by evaporation and the residue dissolved in 40 ml methanol. 5 ml sodium hydroxide solution 50% is added and this is boiled for 30 minutes under reflux. The reaction mixture is evaporated, the residue taken up in dichloromethane, and the organic phase washed with water, then dried and the solvent evaporated. Chromatography on silica gel with ethyl acetate: hexane, 1:10, yields the title compound with a melting point of 101-103° C.

Example H1-5: 2-(2,6-Difluorophenyl)-4-(4'-trifluoromethylbiphenyl-4-yl)-4,5-dihydro-oxazole Dimethoxyethane, tetrahydrofuran and water are degassed for 30 minutes with argon before the start of the reaction. 25 g 2-(2,6-Difluorophenyl)-4-iodophenyl-4,5-dihydrooxazole is suspended in 14.8 g 4-trifluoromethylbenzeneboric acid, 27 g potassium carbonate and 7.5 g Pd(PPh3)4 in 700 ml dimethoxyethane, 400 ml tetrahydrofuran and 700 ml water. Under an argon atmosphere, the mixture is stirred for 3 hours under reflux. After cooling, it is concentrated by evaporation, the residue taken up in ethyl acetate, and the organic phase washed with water and brine, then dried and concentrated by evaporation.

Chromatography on silica gel with dichloromethane yields the title compound. Melting point 148-149° C.

Example H2: Preparation of 2-(2,6-difluorophenyl)-4-(4'-trifluoromethylbiphenyl-4-yl)-4,5-dihydro-oxazole of the formula

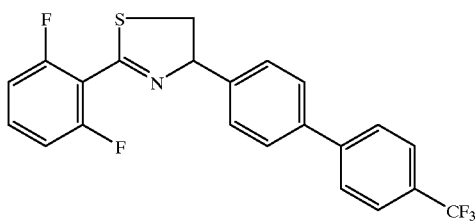

1 g 2-(2,6-Difluorophenyl)-4-(4'-trifluoromethylbiphenyl-4-yl)-4,5-dihydro-oxazole and 0.505 g Lawesson's reagent are added to 15 ml toluene and the mixture stirred for 18 hours at reflux temperature. It is then cooled to 0° C., filtered and the filter residue recrystallized from diethylether/hexan (1:1). This yields the title compound with a melting point of 153-154° C.

Example H3: The other compounds of formula (I) can also be prepared in a manner similar to that in Examples H1 and H2.

| Formulation examples of application in crop protection (% = percentage by weight) | | | |
|---|---|---|---|
| Example F1: Emulsion concentrates | a) | b) | c) |
| Active ingredient | 25% | 40% | 50% |
| Calcium dodecylbenzenesulfonate | 5% | 8% | 6% |
| Castor oil polyethylene glycol ether (36 mol EO) | 5% | — | — |
| Tributyl phenol polyethylene glycol ether (30 mol EG) | — | 12% | 4% |
| Cyclohexanone | — | 15% | 20% |
| Xylene mixture | 65% | 25% | 20% |

EO is the degree of ethoxylation.

Mixing of finely ground active ingredient and adjuvants results in an emulsion concentrate which is diluted with water to yield emulsions of the desired concentration.

| Example F2: Solutions | a) | b) | c) | d) |
|---|---|---|---|---|
| Active ingredient | 80% | 10% | 5% | 95% |
| Ethylene glycol monomethyl ether | 20% | — | — | — |
| Polyethylene glycol (MW 400) | — | 70% | — | — |
| N-Methylpyrrolid-2-one | — | 20% | — | — |
| Epoxidized coconut oil | — | — | 1% | 5% |
| Petrol (boiling limits: 160–190°) | — | — | 94% | — |

MW is the molecular weight.

Mixing of finely ground active ingredient and adjuvants results in a soluble which is suitable for application in the form of fine droplets.

| Example F3: Granulates | a) | b) | c) | d) |
|---|---|---|---|---|
| Active ingredient | 5% | 10% | 8% | 21% |
| Kaolin | 94% | — | 79% | 54% |
| Highly dispersed silicic acid | 1% | — | 13% | 7% |
| Attapulgite | — | 90% | — | 18% |

The active ingredient is dissolved in dichloromethane, the solution sprayed onto the carrier mixture, and the solvent evaporated off under vacuum.

| Example F4: Dusts | a) | b) |
|---|---|---|
| Active ingredient | 2% | 5% |
| Highly dispersed silicic acid | 1% | 5% |
| Talc | 97% | — |
| Kaolin | — | 90% |

Mixing of active ingredient and carriers results in dust ready for use.

| Example F5: Wettable powders | a) | b) | c) |
|---|---|---|---|
| Active ingredient | 25% | 50% | 75% |
| Sodium ligninsulfonate | 5% | 5% | — |
| Sodium lauryl sulfate | 3% | — | 5% |
| Sodium diisobutyl naphthalene sulfonate | — | 6% | 10% |
| Octylphenol polyethylene glycol ether (7–8 mol EO) | — | 2% | — |
| Highly dispersed silicic acid | 5% | 10% | 10% |
| Kaolin | 62% | 27% | — |

Active ingredient and adjuvants are mixed and the mixture ground in a suitable mill. Wettable powders are obtained which can be diluted with water to give suspensions of the desired concentration.

| Example F6: Emulsion concentrate | |
|---|---|
| Active ingredient | 10% |
| Octylphenol polyethylene glycol ether (4–5 mol EO) | 3% |
| Calcium dodecylbenzenesulfonate | 3% |
| Castor oil polyethylene glycol ether(36 mol EO) | 4% |
| Cyclohexanone | 30% |
| Xylene mixture | 50% |

Mixing of finely ground active ingredient and adjuvants results in an emulsion concentrate which is diluted with water to yield emulsions of the desired concentration.

| Example F7: Dusts | a) | b) |
|---|---|---|
| Active ingredient | 5% | 8% |
| Talc | 95% | — |
| Kaolin | — | 92% |

Dust ready for use are obtained by mixing active substance and carrier, then grinding the mixture in a suitable mill.

| Example F8: Extruder granulate | |
|---|---|
| Active ingredient | 10% |
| Sodium ligninsulfonate | 2% |
| Carboxymethylcellulose | 1% |
| Kaolin | 87% |

Active ingredient and adjuvants are mixed, the mixture ground, wetted with water, extruded and granulated, and the granulate dried in a stream of air.

| Example F9: Coating granulate | |
|---|---|
| Active ingredient | 3% |
| Polyethylene glycol (MW 200) | 3% |
| Kaolin | 94% |

Homogenous application of the finely ground active ingredient to the kaolin wetted with polyethylene glycol in a mixer results in dust-free coating granulates.

| Example F10: Suspension concentrate | |
|---|---|
| Active ingredient | 40% |
| Ethylene glycol | 10% |
| Nonylphenol polyethylene glycol ether (15 mol EO) | 6% |
| Sodium ligninsulfonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active ingredient and adjuvants results in a suspension concentrate which is diluted with water to yield suspension of the desired concentration.

Biological Examples:
Examples of use in crop protection
Example B1: Ovicidal effect on *Heliothis virescens*

Eggs of *Heliothis virescens* laid on filter paper are immersed for a short time in an acetonic aqueous test solution containing 400 ppm of the active ingredient to be tested. After drying of the test solution, the eggs are incubated in Petri dishes. After 6 days, the percentage hatching rate of the eggs is compared with that for untreated controls (% reduction in hatching rate).

The instantly claimed compounds show good efficacy in this test. In particular, the compound of Example H1-5 shows a reduction of more than 80%.

Example B2: Effect on *Diabrotica balteata* larvae

Corn seedlings are sprayed with an aqueous emulsion containing 400 ppm of active ingredient. After drying of the spray deposit, the corn seedlings are inoculated with 10 second stage larvae of *Diabrotica balteata* and transferred to a plastic container. Six days later they are evaluated. The percentage reduction of the population (% response) is determined by comparing the number of dead larvae on the treated plants with those on the untreated plants.

The instantly claimed compounds show good efficacy against *Diabrotica balteata* in this test. In particular, the compound of Example H1-5 shows a response of more than 80%.

Example B3: Effect on *Tetranychus urticae*

Young bean plants are inoculated with a mixed population of *Tetranychus urticae* and, one day later, are sprayed with an aqueous emulsion containing 400 ppm of active ingredient. The plants are incubated for 6 days at 25° C. and then evaluated. The percentage reduction of the population (% response) is determined by comparing the number of dead eggs, larvae, and adults on the treated plants with those on the untreated plants. The instantly claimed compounds show good efficacy against *Tetranychus urticae* in this test. In particular, the compound of Example H1-5 shows a response of more than 80%.

Example B4: Effect on *Heliothis virescens* caterpillars

Young soya plants are sprayed with an aqueous emulsion containing 400 ppm of active ingredient. After drying of the spray deposit, the soya plants are inoculated with 10 first stage caterpillars of *Heliothis virescens* and transferred to a plastic container. Six days later they are evaluated. The percentage reduction of the population (% response) is determined by comparing the number of dead caterpillars and the extent of feeding damage on the treated plants with those on the untreated plants.

The instantly claimed compounds show good efficacy against *Heliothis virescens* in this test. In particular, the compound of Example H1-5 shows a response of more than 80%.

Example B5: Effect on *Plutella xylostella* caterpillars

Young cabbage plants are sprayed with an aqueous emulsion containing 400 ppm of active ingredient. After drying of the spray deposit, the cabbage plants are inoculated with 10 third stage caterpillars of *Plutella xylostella* and transferred to a plastic container. Three days later they are evaluated. The percentage reduction of the population (% response) is determined by comparing the number of dead caterpillars and the extent of feeding damage on the treated plants with those on the untreated plants.

The instantly claimed compounds show good efficacy against *Plutella xylostella* in this test. In particular, the compound of Example H1-5 shows a response of more than 80%.

Example B6: Ovocidal/larvicidal effect on *Heliothis virescens*

Eggs of *Heliothis virescens* laid on cotton are sprayed with an aqueous emulsion containing 400 ppm of active ingredient. After 8 days, the percentage hatching rate of the eggs and the survival rate of the caterpillars are compared with those for untreated controls (% reduction of population)

The instantly claimed compounds show good efficacy against *Heliothis virescens*. In particular, the compound of Example H1-5 shows a response of more than 80%.

Example B7: Ovicidal effect on *Tetranychus urticae*

Young bean plants are inoculated with females of *Tetranychus urticae*, which are removed again after 24 hours. The plants colonized with eggs are sprayed with an aqueous emulsion containing 400 ppm of active ingredient. The plants are incubated for 6 days at 25° C. and then evaluated. The percentage reduction of the population (% response) is determined by comparing the number of dead eggs, larvae, and adults on the treated plants with those on the untreated plants.

The instantly claimed compounds show good efficacy against *Tetranychus urticae* in this test. In particular, the compound of Example H1-5 shows a response of more than 80%.

Example B8: Effect on *Panonychus ulmi* (resistant to organophosphates und carbaryl)

Apple seedlings are inoculated with adult females of *Panonychus ulmi*. After seven days, the infected plants are sprayed with an aqueous emulsion containing 400 ppm of the test compound until they are dripping wet, and cultivated in the greenhouse. After 14 days, they are evaluated. The percentage reduction of the population (% response) is determined by comparing the number of dead mites on the treated plants with those on the untreated plants.

The instantly claimed compounds show good efficacy in the above test. In particular, the compound of Example H1-5 shows a response of more than 80%.

Examples of use in (veterinary) medicine

Example B9: In vitro effect on *Boophilus microplus*

Four test series each of 10 engorged female adults of *Boophilus microplus* are stuck to a plastic plate and covered for 1 hour with a wad of cottonwool soaked with an aqueous suspension or emulsion of the test substance. The test is carried out with concentrations of 100, 32, 10, 3.2, 1.0 and 0.32 ppm. The wad of cottonwool is then removed, and the ticks are incubated for 28 days for the eggs to be laid. The effect on *Boophilus microplus* is assessed according to the following 5 criteria:

1. Number of dead females (immobile with black discoloration) before egg deposition;
2. Number of ticks surviving for several days, but no eggs laid;
3. Number of cases in which eggs are laid, but nothing is hatched;
4. Number of cases in which eggs are laid, and from which embryos hatch, but which do not develop into larvae;
5. Number of cases in which embryos hatch, develop into larvae, and do not show any anomalies within 4 weeks. The compounds of formula (I) in this test show the effect described under point 4. The hatching of larvae is completely suppressed by these substances at concentrations of 100, 32, 10 and 3.2 ppm. Even at 1 ppm, a 60 to 90% suppression of the hatching rate is observed. 2-(2,6-Difluorophenyl)-4-(4'-trifluoromethylbiphenyl-4-yl)-4,5-dihydro-oxazole is the most active test substance in this test.

This test is carried out with both the BIARRA and the ULAM strain, and the results in both cases are identical.

Example B10: In vitro effect on *Dermanyssus gallinae*

Ten engorged female mites of the genus *Dermanyssus gallinae* fixed on a plastic adhesive film are brought into contact with 50 µl of an aqueous suspension or emulsion of the test substance. The test is carried out with concentrations of 32, 10, 3.2, 1.0, 0.32 to 0.0001 ppm. After drying, the film is stuck onto a glass disc. This creates a kind of air bubble around each mite, the lower surface of which is formed by the glass disc and the upper surface by a bulging of the adhesive film. This bubble contains sufficient air for the mite to avoid suffocating. After 5 days, the effect of the test substance is evaluated with the aid of a stereomicroscope by assessing the effect on mortality, egg deposition, egg quality, hatching rate, pupation rate, and development of protonymphs according to the following 4 criteria:

1. if 9 to 10 mites are dead, this indicates a lethal effect;
2. if 2 or more mites survive, but do not produce any eggs, this indicates sterility;
3. if 2 or more mites survive and produce eggs, but no larvae hatch from these eggs and no protonymphs develop, this indicates a development-inhibiting effect;
4. if 2 or more mites survive and lay the usual number of normal eggs, from which larvae hatch and develop into protonymphs, this indicates no activity.

The compounds of formula (I) in this test show the effect described under point 3. They completely inhibit the development of protonymphs at concentrations of 32 to 0.1 ppm. Even when diluted to 0.0032 ppm, the compounds show a 60 to 90% reduction in protonymph development. 2-(2,6-Difluorophenyl)-4-(4'-trifluoromethylbiphenyl-4-yl)-4,5-dihydro-oxazole is the most active test substance in this test.

Example B11: In vitro effect on Australian sheep blowfly *Lucilia cuprina*

In a test tube, 4 ml of a culture medium suitable for blowfly larvae on an agar base is liquefied by heating and mixed with 10 ml of a suspension or emulsion of the test solution. The mixture is left to cool and becomes a solidified culture medium. Test tubes are prepared containing test substances in concentrations of 10, 3.2, 1 and 0.32 ppm. The solidified culture medium is inoculated with 30 to 50 freshly laid eggs of the *Lucilia cuprina* blowfly, the test tubes are loosely closed with a wad of cottonwool, and cultivated in an incubator at 26 to 28° C. After 4 days, the test tubes are taken from the incubator and the larvicidal effect of the test substances is determined. If large vital larvae in the third stage of development are found in a culture medium which is now liquefied and brownish, this indicates an absence of larvicidal effect. By contrast, if the culture medium is not discoloured and remains solidified, and no larvae are found, this indicates 100% larvicidal activity. The compounds of formula (I) in this test show a 100% larvicidal effect on blowflies in all test concentrations.

Example B12: In vitro effect on eggs, larvae or pupae of the cat flea *Ctenocephalides felis*

Acetonic test solutions are prepared containing test substances in concentrations of 15, 1.5, 0.15 and 0.015 ppm. 9.9 ml of each test solution is mixed with 14.85 g of culture medium for flea larvae and dried for about 12 hours. The slightly clumped, dry culture medium is mechanically pulverized again until it is homogeneous and free-flowing. It is then transferred to bottles for the breeding of fleas. To each bottle, 100 to 200 flea eggs are added, the bottles are loosely closed with a wad of cottonwool and placed in an incubator at 25 to 26° C. and a relative humidity of about 60%. After 21 days, the effect of the test substances in the different concentrations is evaluated and the lowest effective concentration determined using a stereomicroscope. The activity is evaluated on the basis of the hatching rate, larva development, pupation, and the hatching of young fleas. The compounds of formula (I) show a pronounced effect in this test. Up to a dilution of 10 ppm, the development of young fleas is shown to be completely suppressed.

Example B13: In vitro effect on *Haemonchus contortus* in the development of third stage larvae 2 µl of a 5% solution of the test substance in DSMO or methanol is diluted with a further ml of solvent and test tubes wetted on the inside with the solution. After drying, 2 ml agar is added to each test tube. Each test tube is now inoculated with 100 fresh *Haemonchus contortus* eggs in deionized water, the test tubes are loosely closed with a wad of cottonwool and placed in an incubator at 34 to 36° C. and a relative humidity of about 60 to 100%. 24 hours after hatching of the larvae, 30 µl of a culture medium for bacteria is added so that the bacteria introduced with the eggs can reproduce. The volume of water should be such that the test tubes are about one third full. The effect is assessed on the basis of the hatching rate, the development of third stage larvae, the paralysis or death of larvae, or of other development stages. The compounds of formula (I) in this test show a marked development-inhibiting effect. Up to a dilution of 32 ppm, the development of third stage larvae is shown to be completely suppressed.

Example B14: In vivo effect of topical treatment on infestation with mouse fur mites Mice infested with mites (*Myocopetes musculinus* and *Myobia musculi*) are anaesthetized, and the density of the mite population is examined under a stereomicroscope. The mice are divided into groups with the same infection index, i.e. with the same mite population in each case, the index consisting of a scale from 1 (no mites) to 30 (greatest mite density). For test purposes, only mice with an index of at least 25 on the said scale (high mite density) are used. The test substance is applied in the form of a pour-on solution, suspension or emulsion, i.e. applied topically to the fur. The dose is in the range 32 to 0.1 mg/kg bodyweight. Per mouse, 150 μl of solution, suspension or emulsion is applied along the topline of the mouse. Efficacy is evaluated 7, 28 and 56 days after application by comparing the infection index after treatment with that before treatment. The efficacy is expressed as a percentage reduction of the mite population. The compounds of formula (I) in this test show a reduction in mite infestation of more than 80% at concentrations up to 10 mg/kg bodyweight.

Example B15: In vivo effect against infestation with mouse fur mites after subcutaneous injection Mice infested with mites (*Myocopetes musculinus* and *Myobia musculi*) are anaesthetized, and the density of the mite population is examined under a stereomicroscope. The mice are divided into groups with the same infection index, i.e. with the same mite population in each case, the index consisting of a scale from 1 (no mites) to 30 (greatest mite density). For test purposes, only mice with an index of at least 25 on the said scale (high mite density) are used. The test substance is dissolved in a 2:3 mixture (volume/volume) of glycerol formal and polyethylene glycol and injected subcutaneously into the test animals. The dose is in the range 20 to 0.1 mg/kg bodyweight. Efficacy is evaluated 7, 28 and 56 days after application by comparing the infection index after treatment with that before treatment. The efficacy is expressed as a percentage reduction of the mite population. The compounds of formula (I) in this test show a reduction in mite infestation of more than 80% at concentrations as low as 0.32 mg/kg bodyweight. The mice, however, do not show skin irritations at the injection site or any other unwanted side effects. The substances are shown to be very well tolerated.

What is claimed is:

1. A compound of formula

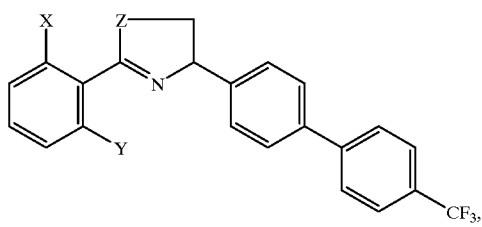

(I)

wherein X and Y are, independently of one another, fluorine or chlorine, and Z is O or S;

and where appropriate their possible tautomers, in each case either in free form or in the form of a salt.

2. A compound of formula (I) according to claim 1, wherein X and Y are fluorine.

3. A compound of formula (I) according to claim 1, wherein Z is O.

4. A method for preparing the compounds of formula (I) according to claim 1 and where appropriate their tautomers, in each case in free form or in the form of a salt, comprising a) the reaction of a compound of formula

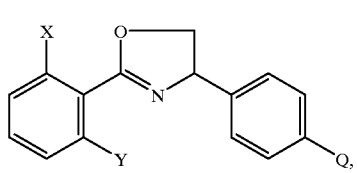

(II)

wherein X and Y are as defined for formula (I) and Q is bromine or iodine, with a compound of formula

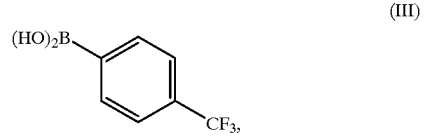

(III)

and b) where appropriate, for preparing a compound of formula (I), wherein Z is S, the reaction of the resulting compound of formula (I), wherein Z is O, with [2,4-bis(methoxyphenyl)-1,3-dithia-2,4-diphosphetane-2,4-disulfide] or with phosphorus pentasulfide;

and in each case, if so desired, the conversion of a compound of formula (I) obtainable according to the method or by other means, or a tautomer thereof, present in free form or in the form of a salt, into a different compound of formula (I) or a tautomer thereof, the separation of a mixture of isomers obtainable according to the method and isolation of the desired isomers and/or the conversion of a free compound of formula (I) obtainable according to the method, or a tautomer thereof, into a salt, or a salt obtainable according to the method from a compound of formula (I), or a tautomer thereof, into the free compound of formula (I), or a tautomer thereof, or into a different salt.

5. A pesticidal composition comprising at least one compound of formula (I) according to claim 1 as active ingredient, either in free form or in the form of an agrochemically acceptable salt, and at least one adjuvant.

6. A method for the control of pests comprising applying a composition of claim 5 to the pests or their habitat.

7. A method according to claim 6 for the control of insects and members of the order acarina.

8. A method for preparing a composition of claim 5 which contains at least one adjuvant and comprises the intimate mixing and/or grinding of the active ingredient with the adjuvant(s).

9. A method of protecting a plant propagation material from a pest, comprising treating said propagation material or the cultivation area for said propagation material with a pesticidal composition of claim 5.

10. The method of claim 9 wherein said plant propagation material is treated.

11. A composition to combat ectoparasites or endoparasites in humans or animals, comprising a compound of claim 1 and a physiologically acceptable adjuvant.

12. The method of claim 6 wherein said habitat is a plant propagation material or a cultivation area for said plant propagation material.

13. The method of claim 12 wherein said habitat is a plant propagation material.

* * * * *